(12) United States Patent
Wong

(10) Patent No.: US 9,017,968 B2
(45) Date of Patent: Apr. 28, 2015

(54) MEANS AND METHODS FOR PRODUCING AUTHENTIC HUMAN BASIC FIBROBLAST GROWTH FACTOR

(71) Applicant: Gene-Vinate Limited, Clear Water Bay (HK)

(72) Inventor: Wan Keung Raymond Wong, Clear Water Bay (HK)

(73) Assignee: Gene-Vinate Limited, Clear Water Bay (HK)

( * ) Notice: Subject to any disclaimer, the term of this patent is extended or adjusted under 35 U.S.C. 154(b) by 0 days.

(21) Appl. No.: 13/672,853

(22) Filed: Nov. 9, 2012

(65) Prior Publication Data

US 2014/0134673 A1    May 15, 2014

(51) Int. Cl.
C12P 21/04    (2006.01)
C07K 14/50    (2006.01)

(52) U.S. Cl.
CPC ..................... *C07K 14/50* (2013.01)

(58) Field of Classification Search
None
See application file for complete search history.

(56) References Cited

U.S. PATENT DOCUMENTS

| | | |
|---|---|---|
| 5,223,407 A | 6/1993 | Wong et al. |
| 5,646,015 A | 7/1997 | Wong et al. |
| 7,517,528 B2 | 4/2009 | Wong et al. |

FOREIGN PATENT DOCUMENTS

EP    0237966 A2 * 9/1987

OTHER PUBLICATIONS

Li et al., Microbial Cell Factories, 2012, vol. 11, pp. 1-10.*
Schnaitman, Journal of Bacteriology, 1971, vol. 108, p. 553-563.*
Mirzahoseini et al., World Journal of Microbiology & Biotechnology, 2004, vol. 20, pp. 161-165.*
Semple-Rowland et al., Molecular Vision, 2010, vol. 16, pp. 916-934.*
Yansura et al., PNAS, 1984, vol. 81, pp. 439-443.*
Wang et al., Research Journal of Biotechnology, 2010, vol. 5, pp. 5-13.*
Nagarajan et al., Gene, 1992, vol. 114, pp. 121-126.*
"Biocompare | The Buyer's Guide for Life Scientists." *Basic fibroblast growth factor*. Biocompare, Web. Accessed on Nov. 28, 2012. <http://www.biocompare.com>.
"Recombinant Human FGF-basic/145aa (carrier-free)." *10 A Decade of Discovery BioLegend*. Biolegend, 2012. Web. Accessed on Nov. 28, 2012. <http://www.biolegend.com>.
"Fibroblast Growth Factor basic, human recombinant (mg qty.)." *Millipore*. 2012. Web. Accessed on Nov. 28, 2012. <www.millipore.com>.
"FGF 2 Sf9 recombinant protein :: FGF 2 Sf9." *My BioSource.com Antibody-Protein-Elisa Kit*. Dec. 2006. Web. Accessed on Nov. 28, 2012. <www.mybiosource.com>.
"FGF2 (NM_002006) Purified Human Protein." *OriGene*. 2012. Web. Accessed on Nov. 28, 2012. <www.origene.com>.
Lam et al., "Enhancement of extracellular production of a Cellulomonas fimi exoglucanase in *Escherichia coli* by the reduction of promoter strength" *Enzyme and Microbial Technology*, vol. 20, May 15, 1997, pp. 482-488.
McGee M.D. et al., "Recombinant basic fibroblast growth factor accelerates wound healing." Abstract *Journal of Surgical Research*. vol. 45, Issue 1, Jul. 1988, pp. 145-153. (Available online Feb. 9, 2004. Presented at the Annual Meeting of the Association for Academic Surgery, Orlando, Florida, Nov. 1-4, 1987.).
Mirzahoseini et al., "Differential expression of human basic fibroblast growth in *Escherichia coli*: potential role of promoter." *World Journal of Microbiology & Biotechnology*. vol. 20, 2004, pp. 161-165.
Mu et al., "High-level expression, purification, and characterization of recombinant human basic fibroblast growth factor in *Pichia pastoris*." *Protein Expression and Purification*. vol. 59, 2008, pp. 282-288.
Alibolandi et al., "Purification and Refolding of Overexpressed Human Basic Fibroblast Growth Factor in *Escherichia coli*." *Biotechnology Research International*, vol. 2011, pp. 1-6.
Andrades et al., "Production of a recombinant human basic fibroblast growth factor with a collagen binding domain." *Protoplasma*. Springer-Verlag 2001, vol. 218 pp. 95-103.
Bae et al., "The YSIRK-G/S Motif of *Staphylococcal* Protein A and Its Role in Efficiency of Signal Peptide Processing." *Journal of Bacteriology*, May 2003, vol. 185, No. 9 pp. 2910-2919.
Barr et al., "Expression and Processing of Biologically Active Fibroblast Growth Factors in the Yeast *Saccharomyces cerevisiae*." *The Journal of Biological Chemistry*, 1988, vol. 263, No. 31, Issue of Nov. 5, pp. 16471-16478.
Bikfalvi et al., "Biological Roles of Fibroblast Growth Factor-2." *Endocrine Reviews*, vol. 18, No. 1, 1997, pp. 26-45.
Ferrer-Miralles et al., "Microbial factories for recombinant pharmaceuticals", *Microbial Cell Factories*, 2009, 8:17, 8 pages.
Garke et al., "Preparative two-step purification of recombinant human basic fibroblast growth factor from high-cell-density cultivation of *Eschericia coli*." Journal of Chromatography B, 737, 2000, pp. 25-38.
Haldenwang, W.G. "The sigma factors of *Bacillus subtilis*." *Microbiological Reviews*. Mar. 1995, pp. 1-30.
Huang et al., "Human epidermal growth factor excreted by recombinant *Escherichia coli* K-12 has the correct N-terminus and is fully bioactive." Process Biochemistry 35, 1999, pp. 1-5.
Khurana et al., "Insights from Angiogenesis Trials Using Fibroblast Growth Factor for Advanced Arteriosclerotic Disease." Trends Cardiovasc Med, vol. 13, 2003, pp. 116-122.
Kontaridis et al., "Role of SHP-2 in Fibroblast Growth Factor Receptor-Mediated Suppression of Myogenesis in C2C12 Myoblasts." *Molecular and Cellular Biology*, Jun. 2002, pp. 3875-3891.
Lam et al., "Construction of an efficient *Bacillus subtilis* system for extracellular production of heterologous proteins." Journal of Biotechnology, 63, 1998, pp. 167-177.

(Continued)

*Primary Examiner* — Michele K Joike
*Assistant Examiner* — Mindy G Brown
(74) *Attorney, Agent, or Firm* — Heslin Rothenberg Farley & Mesiti P.C.; Andrew K. Gonsalves, Esq.

(57) ABSTRACT

The present invention is concerned with an engineered biological system for production of authentic human basic fibroblast growth factor (hbFGF). The system makes use of a bacterial host and has a recombinant DNA construct with an insert. The insert contains a first VegC promoter, $lac^q$ operator, a second VegC promoter and DNA coding for human basic fibroblast growth factor.

11 Claims, 3 Drawing Sheets

(56) References Cited

OTHER PUBLICATIONS

Nakayama et al., "Efficient secretion of the authentic mature human growth hormone by *Bacillus subtilis*." *Journal of Biotechnology*, vol. 8, Issue 2, 1988, pp. 123-134.

Palva, et al., "Secretion of interferon by *Bacillus subtilis*." *Gene*, vol. 22, 1983 pp. 229-235.

Rose, Ronald E., "The nucleotide sequence of pACYC184." *Nucleic Acids Research*, vol. 16 No. 1, 1988, p. 355.

Schägger et al., "Tricine-Sodium Dodecyl Sulfate-Polyacrylamide Gel Electrophoresis for the Separation of Proteins in the Range from 1 to 100 kDa." Analytical Biochemistry, vol. 166, 1987, pp. 368-379.

Sellke et al., "Therapeutic Angiogenesis With Basic Fibroblast Growth Factor: Technique and Early Results." *The Annals of Thoracic Surgery*, vol. 65, 1998, pp. 1540-1544.

Simonen et al., "Protein secretion in *Bacillus* species." *Microbiological Reviews*, vol. 57 No. 1, 1993, pp. 109-137.

Sivakesava et al., "Production of excreted human epidermal growth factor (hEGF) by an efficient recombinant *Escherichia coli* system." Process Biochemistry, vol. 34, 1999, pp. 893-900.

Tsang et al., "Human Epidermal Growth Factor Enhances Healing of Diabetic Foot Ulcers." *Diabetes Care*, vol. 26, No. 6, Jun. 2003, pp. 1856-1861.

Tsang et al., "The use of recombinant human epidermal growth factor (rhEGF) in a gentleman with drug-induced Steven Johnson syndrome." *Dermatology Online Journal*, vol. 10, (1): 25, 2004.

Wang et al., "Efficient *Bacillus subtilis* Promoters for Graded Expression of Heterologous Genes in *Escherichia coli*." Research Journal of Biotechnology, vol. 5(4), Nov. 2010, pp. 5-14.

Westers et al., "*Bacillus subtilis* as cell factory for pharmaceutical proteins: a biotechnological approach to optimize the host organism." *Biochimica et Biophysica Acta*, 1694, 2004, pp. 299-310.

Westers et al., "Secretion of functional human interleukin-3 from *Bacillus subtilis*." Journal of Biotechnology, vol. 123, 2006, pp. 211-224.

Wong, Sui-Lam, "Advances in the use of *Bacillus subtilis* for the expression and secretion of heterologous proteins." *Current Opinion in Biotechnology*, vol. 6, 1995, pp. 517-522.

Wong et al., "Engineering and production of streptokinase in a *Bacillus subtilis* expression-secretion system." *Applied and Environmental Microbiology*, vol. 60(2), 1994, pp. 517-523.

Wong et al., "Extracellular expression of human epidermal growth factor encoded by an *Escherichia coli* K-12 plasmid stabilized by the yt12-incR system of *Salmonella typhimurium*." Journal of Industrial Microbiology & Biotechnology, vol. 21, 1998, pp. 31-36.

Wong et al., "Engineering of Efficient *Escherichia coli* Excretion Systems for the Production of Heterologous Proteins for Commercial Applications." *Recent Patents on Chemical Engineering*, vol. 5, 2012, pp. 45-55.

Wu et al., "Basic fibroblast growth factor expressed in *Bacillus subtilis* B5224." Letters in Biotechnology, vol. 13, No. 6, Nov. 2002, pp. 439-442.

Xu et al., "Basic Fibroblast Growth Factor Supports Undifferentiated Human Embryonic Stem Cell Growth Without Conditioned Medium." Stem Cells, vol. 23, 2005, pp. 315-323.

* cited by examiner

(A)
Anti-Phosphotyrosine

(B) Anti-FRS2α

MEANS AND METHODS FOR PRODUCING AUTHENTIC HUMAN BASIC FIBROBLAST GROWTH FACTOR

SEQUENCE LISTING

The instant application contains a Sequence Listing which has been submitted in ASCII format via EFS-Web and is hereby incorporated by reference in its entirety. Said ASCII copy, created on Sep. 24, 2012, is named G02001US.txt and is 9,961 bytes in size.

FIELD OF THE INVENTION

The present invention is concerned with means and methods for producing authentic human basic fibroblast growth factor (hbFGF), and in particular but not limited to using *Bacillus subtilis* as machinery for excreting authentic hbFGF for collection in supernatant of the culture of *Bacillus subtilis*.

BACKGROUND OF THE INVENTION

Studies have shown that human basic fibroblast growth factor (hbFGF) has a wide range of medical and cosmetic applications. For instance, hbFGF can be used to treat various hard to heal wounds such as diabetic foot ulcers which would otherwise require foot amputation. However, producing hbFGF in the past had encountered many difficulties. For example, producing hbFGF in a large scale had not been possible because the quantities that could be produced were too low to be commercially or realistically justifiable. Even when a small quantity of hbFGF was produced, due to different known or unknown reasons, the hbFGF produced was often either un-authentic or lack bioactivity. Because of these difficulties, commercially available hbFGF is very costly. At the time of fling this patent application, a mere mature-hbFGF analogue is sold in the market at an unaffordable rate of over US$1 million per gram. Whether such analogue would yield sufficient bioactivity similar to an authentic-hbFGF is yet another issue.

The present invention seeks to address the aforementioned difficulties, or at least to provide an alternative to the general public.

SUMMARY OF THE PRESENT INVENTION

According to a first aspect of the present invention, there is provided an engineered biological system for production of authentic human basic fibroblast growth factor (hbFGF) using a bacterial host, comprising a recombinant DNA construct with an insert including, in sequence of, a first VegC promoter, $lac^q$ operator, a second VegC promoter and DNA coding for human basic fibroblast growth factor.

Preferably, the system may comprise a neutral protease leader sequence (NPR), and the neutral protease leader sequence is positioned between the second VegC promoter and the DNA coding for human basic fibroblast growth factor.

In an embodiment, the recombinant DNA construct may reside in a bacterium of *Bacillus subtilis*.

According to a second aspect of the present invention, there is provided a method for production of authentic human basic fibroblast growth factor (hbFGF), comprising a) preparing a recombinant DNA construct with an insert including a first VegC promoter, $lac^q$ operator, a second VegC promoter and DNA coding for human basic fibroblast growth factor, and b) introducing said DNA construct in a host for expression of the human basic fibroblast growth factor.

Preferably, the method may comprise a step of facilitating export of the human basic fibroblast growth factor to culture in which the *Bacillus subtilis* suspends.

In an embodiment, the method may comprise a step of positioning a neutral protease leader sequence (NPR) between the second VegC promoter and the DNA coding for human basic fibroblast growth factor. In a specific embodiment, the insert may consist of, sequentially, the first VegC promoter, the $lac^q$ operator, the second VegC promoter, the neutral protease leader sequence and the DNA coding for human basic fibroblast growth factor. In a preferred embodiment, the host is *Bacillus subtilis*.

In one embodiment, the method may comprise a step of, during the production of the authentic human basic fibroblast growth factor, treating the host with lysozyme. Preferably, treatment of the host with the lysozyme may be conducted when the host is at its log growth phase. The host may be treated with 0.024-0.1 mg/ml of the lysozyme.

In another embodiment, the method may comprise a step of treating the host with Triton X-100. Preferably, treatment of the host with the Triton X-100 may be performed during stationary-phase of the host. The host may be treated with 0.025%-0.08% mg/ml of the Triton X-100.

Advantageously, the method may comprise, without having to concentrate the culture, a step of harvesting from 30-43 mg/l of the human basic fibroblast growth factor from the culture. In many cases, the human basic fibroblast growth factor harvested from the culture may be at least 40 mg/l. This would be approximately a 10-fold increase compared to other methodologies.

According to a third aspect of the present invention, there is provided a method for facilitating collection of heterologous proteins secretable by a engineered biological system, comprising a step of treating the biological system, during production of the heterologous proteins, an effective amount of lysozyme and/or an effective amount of Triton X-100, wherein treatment with the lysozyme is performed during log growth phase of the host and/or treatment with the Triton X-100 is performed during stationary-phase of said host.

Advantageously, the biological system may be *Bacillus subtilis*.

Preferably, the effective amount of the lysozyme may be 0.025-0.1 mg/ml. The effective amount of the Triton X-100 may be 0.025-0.08%.

In a preferred embodiment, treatment by the lysozyme or the Triton X-100 may last for at least 2 hours.

BRIEF DESCRIPTION OF THE DRAWINGS

Some embodiments of the present invention will now be explained, with reference to the accompanied drawings, in which:—

DESCRIPTION OF DETAILED OF PREFERRED EMBODIMENTS OF THE INVENTION

Figure 1:
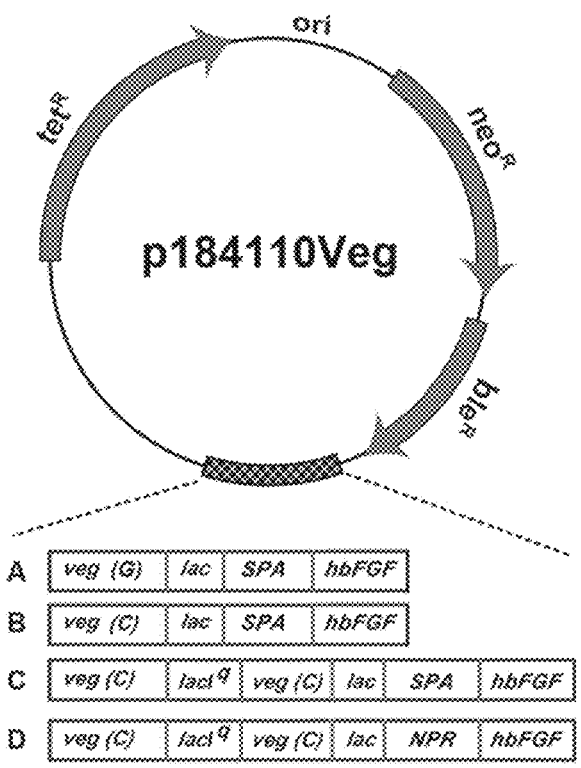
FIG. 1 is a diagram illustrating different embodiments of DNA constructs according to the present invention.

Protein production making use of bacterial host is often unpredictable in that many different factors can play in the process. For example, a bacterial host which would be suitable in producing a certain protein would not necessarily be suitable in producing other proteins. Similarly, an engineered DNA construct carried in a host which would cause the host in producing a certain protein efficiently would not necessarily be suitable for use in other hosts. Studies leading to the present invention has identified certain host and/or engineered DNA constructs which would be particular advantageously or efficient in producing certain proteins. Specifically, in embodiments according to the present invention, Bacillus subtilis and/or the use of an engineered DNA construct have been shown to be able to express authentic mature human basic fibroblast growth factor (hbFGF) at a commercially acceptable quantity.

In order appreciate the present invention, it is to be noted that Bacillus subtilis has been considered a favorable host system for use in secretory production of heterologous proteins. There have been a few human proteins of medical interest, which include interleukins, interferons, growth hormone and epidermal growth factor, reported to be expressed using B. subtilis as the host. Nevertheless, probably due to low production efficiency and high production costs, these proteins have never been produced using B. subtilis for drug applications. During the course leading to the present invention, studies and experiments were conducted to use B. subtilis as a producer for medically valuable proteins. One of these proteins is human epidermal growth factor (hEGF), which has been shown to be effective in treating various hard-to-heal wounds including diabetic foot ulcers, Stevens-Johnson syndrome and bedsores. However, difficulties were encountered in that despite being able to express hEGF in B. subtilis to some extent, the production efficiency did not justify the use of B. subtilis in view of other possible alternatives on host such as Escherichia coli.

Studies leading to the present invention were conducted by engineering an extracellular E. coli system for large-scale production of authentic hEGF. However, in attempting to use E. coli and the same approach to express authentic mature human basic fibroblast growth factor {Mat-hbFGF; a 16.5 kDa, non-glycosylated, 146 amino acid}, an unauthentic derivative rather than an authentic Mat-hbFGF was obtained. There are both known and unknowns reasons leading to the inability of using E. coli as a host. These reasons include problems of proteolysis, acetylation, and formation of inclusion bodies. As a result, structurally different variants of Mat-hbFGF were obtained. Studies leading to the present invention were also performed to explore the possibility of expressing authentic Mat-hbFGF using a fusion approach; however, the manufacturing costs associated with such approach were unrealistically too high. Due to a wide variety of clinical applications of Mat-hbFGF, e.g. in therapeutic angiogenesis and cultivation of human embryonic stem cells, and the high production costs of using convention approaches, at the time of preparing this patent application the current market price for Mat-hbFGF is astonishingly high. Even just a Mat-hbFGF analogue is sold at an unaffordable rate of over US$ 1 million per gram.

The present invention is concerned with different aspects of protein expression and/or secretion. One of the aspects is concerned with the application of novel fine-tuned Veg-cassette vectors for secretory expression of various proteins in B. subtilis. In this aspect, constructs comprising such vector were used to enable expression of the hbFGF and secretion of the protein into the culture medium. A refined shake-flask culture protocol was shown not only able to attain an impressive expression of 40 mg l$^{-1}$ of hbFGF, but also a biologically active hbFGF product characterized to possess an authentic structure. Experiments showing the choice of bacterial host in protein production, construction of recombinant DNA construct, expression and secretion of the protein and/or treatment of the bacterial host during protein productions are illustrated below.

Experiments

Methods

Bacterial Strain & Chemicals

The B. subtilis strain 1A751 (eglSΔ102, bglTlbglSΔEV, npr,apr, his) used in this study was obtained from the Bacillus Genetics Stock Centre at Ohio. The Phusion PCR Kit, restriction and modifying enzymes were purchased from New England Biolabs (Ipswich, Mass., USA). All primers were purchased from Invitrogen (Carlsbad, Calif.). Other chemicals were purchased from Sigma-Aldrich Corporation (St. Louis, Mo., USA) unless otherwise specified. Anti-hbFGF serum was raised in rabbit.

Construction of hbEGF Expression Constructs

The p184110Veg vector was derived from the B. subtilis/E. coli shuttle vector, pM2Veg, with the following modifications. The XmnI-EcoRI fragment of pM2 containing the origin of replication (ori) of ColEI and the bla gene was replaced by a PvuII-AvaI fragment obtained from pACYC184, which carried the ori of plasmid p15A and the tetracycline-resistance (tet) gene of pSC101. Please see FIG. 1. The hbfgf gene (GenBank: AAV70487.1) was synthesized by overlap extension PCR using 10 oligo primers P1-P10. Please see Table 1 and Sequence Listing for primers SEQ ID NOs. 1-10 used in this study.

It was then precisely fused with the Staphylococcal Protein A (SPA) secretion leader sequence harbored in two expression cassettes, the VegG and VegC cassettes, using P10-P13 (Sequence Listing for primers SEQ ID NOs. 10-13) as mutagenic primers. Both resultant products were cut with KpnI and PstI, cloned into pUC18, and then cut with EcoRI and HindIII to form the inserts. Plasmid p184110Veg was cut with EcoRI and SmaI, and religated with the two inserts to form hbFGF expression constructs: pVegGbFGF and pVegCbFGF (FIG. 1). To construct the IPTG inducible pCCQ plasmid, the lacI$^q$ gene was inserted into pVegCbFGF as follows. Firstly, the HindIII fragment containing the lacI$^q$ gene was isolated from pMMB22 and cloned into pUST6 restricted with HindIII to form pUST6IQ. To facilitate transcription of the lacI$^q$ gene in B. subtilis, a fragment containing the vegC promoter and the Bacillus consensus ribosomal binding site (RBS) (Product 1) was first formed by annealing primer A with primer B (Sequence Listing for primers SEQ ID NOs. 17-18). A 0.36-kb PCR fragment containing the 5'-terminal region of the lacI$^q$ gene (Product 2) was then amplified using primers C and D (Table 1), with pUST6IQ as the template. A PCR fusion product containing the vegC promoter, the Bacillus consensus RBS and the 5'-terminal region of the lacI$^q$ gene was generated by overlap extension using Products 1 and 2 as templates, and primers A and D (Sequence Listing for primers SEQ ID NOs. 17-20) for amplification. The PCR product was digested with BamHI and MluI, and the insert was then cloned into pUST6IQ digested with the same endonucleases to form pUST6VegCIQ. Secondly, an EcoRI fragment harboring the lacI$^q$ gene placed under the control of the vegC promoter obtained from pUST6VegCIQ was cloned into the unique EcoRI site on pVegCbFGF to form plasmid pCCQ. Plasmid pSO, which employed the NPR leader sequence of a *B. amyloliquefaciens* protease gene to facilitate hbFGF secretion, was constructed by first performing overlap extension PCR using pCCQ as the template and P10, P14-P16 as primers (Sequence Listing for primers SEQ ID NOs. 10-13), followed by EcoRI plus PstI restriction and religation. All plasmid constructions were confirmed by DNA sequencing.

Cell Culture Techniques

To cultivate *B. subtilis* transformants, a seed culture was first prepared by growing a fresh colony of cells in 50 ml 2×LB medium (2% Tryptone, 1% yeast extract, 2% NaCl) supplemented with 20 μg ml$^{-1}$ of kanamycin at 37° C., 250 rpm until an $A_{600}$ value was 2. Various concentrations of lysozyme, Triton X-100 and IPTG (details described in further description of FIG. 5) were added to the culture, which was then allowed to continuously grow for various time intervals. Subsequently, the culture medium was collected by spinning down the cells. The cell pellet was re-suspended and incubated in 0.5 mL of TSM solution (50 mM TrisHCl [pH 7.5], 10 mM MgCl$_2$, 0.5 M sucrose)$^{40}$ supplemented with 0.1 mg ml$^{-1}$ lysozyme for 15 min at 37° C. The supernatant composed of the peptidoglycan, was collected by spinning down the cells. The pellet was dissolved in 0.2 ml of lysis buffer (10 mM K$_2$HPO$_4$—KH$_2$PO$_4$, 7.5 mM MgCl$_2$, 1% sucrose, 1 mg ml$^{-1}$ lysozyme) and incubated for 30 min at 37° C., and subsequently boiled for 10 min at 100° C. to obtain the cell lysate. The fractions were analyzed for hbFGF by Western blotting, and densitometry of Western blot images were quantified using ImageJ software (NIH).

Purification of rhbFGF

Culture supernatant was collected and filtered through a 0.45-μm filter. The filtrate was passed through a column packed with heparin-agarose beads (BioRad Laboratories, Hercules, Calif.) equilibrated with 50 mM Tris HCl [pH 7.5]. The column was then washed thoroughly with Tris-NaCl buffer (50 mM Tris HCl, 0.2 M NaCl), and hbFGF was eluted with a linear gradient of NaCl (0.3 M-2.5 M).

Liquid Chromatography Tandem Mass Spectrometry

The purified hbFGF was electrophoresed on a Tricine-SDS 15% gel, and the gel band containing hbFGF was excised, washed, and incubated with 1 μg trypsin dissolved in 50 mM NH$_4$HCO$_3$ on ice overnight. Hydrolyzed samples were analyzed by the LTQ Velos Linear Ion Trap Mass Spectrometer (Thermo Fisher Scientific, San Jose) coupled with an online Accela HPLC and an Electron Transfer Dissociation (ETD) source utilizing nanospray ionization. Peptides were first enriched with a Zorbax 300SB C18 column (5 um, 5×0.3 mm, Agilent Technologies, Santa, Calif.), followed by passing through a BioBasic-18 column (150×0.1 mm) packed with C18 material (5 um particle size). Mobile phase A (0.1% formic acid) and mobile phase B (100% acetonitrile) were used to establish a 80-min gradient comprised of: 0-5 min of 2% B, 8 min of 2-8% B, 12 min of 8-13% B, 21 min of 13-25% B, 14 min of 25-45% B, and 3 min of 45-80% B, followed by maintenance at 80% B for 7 min, and re-equilibration at 2% B for 10 min. The MS was operated in a data-dependent mode. A sample was injected into the MS with an electrical potential of 1.8 kV and ion transfer tube temperature set at 250° C. A full survey MS scan (300-2000 m/z range) was acquired. Five most intense ions were selected for collision-induced dissociation (CID) in MS/MS. For CID, the activation Q was set at 0.25, isolation width (m/z) at 2.0, activation time for 10 miniseconds, and normalized collision energy of 35%. Mascot search engine (Matrix science, Boston, Mass.) was employed to facilitate protein identification.

Biological Assay of hbFGF

The use of hbFGF to stimulate C2C12 myoblasts to form tyrosyl-phosphorylated FRS-2α was performed essentially the same as described previously. In summary, eight aliquots of 1 ml confluently grown C2C12 cells, which shared the same cell density, were grown on 8 new plates with each containing one ml of fresh medium (DMEM+10% FBS). The next morning, the medium was replaced by DMEM+0.4% FBS and the cells were starved for 6 hr. Afterwards, the cells were incubated at 37° C. and 5% CO$_2$ for 50 min separately with different quantities of: 1) DMEM, 10 μM Na$_3$VO$_4$ and recombinant Mat-hbFGF; 2) DMEM, 10 μM Na$_3$VO$_4$ and commercial rhbFGF (147 aa derivative, procured from R&D Systems, Abingdon, UK); 3) a *B. subtilis* culture supernatant sample containing the CenA endoglucanase of *Cellulomonas fimi*. Subsequent to cell lysis, FRS-2α was immunoprecipitated and analyzed by Western blotting with anti-phosphotyrosine and anti-FRS-2α antibodies (Milliopore, Billerica, Mass.).

Further Description of Figures

FIG. 1: Schematic Representation of DNA Constructs Expressing hbFGF

The top diagram shows vector p184110Veg (5.6 kb) whereas additional genetic components of its derivatives: (A) pVegGbFGF, 6.3 kb; (B) pVegCbFGF, 6.3 kb; (C) pCCQ, 7.6 kb; and (D) pSO 7.6 kb; constructed for secretory expression of hbFGF are depicted underneath. Symbols for genetic elements shown in p184110Veg and its derivatives are: ori=origin of replication for replication in *B. subtilis*; tet$^R$, ble$^R$ and neo$^R$ representing structural genes conferring resistance to tetracycline, bleomycin and neomycin, respectively; hbFGF: hbFGF gene; lacI$^q$: coding sequence for the overexpressed Lac repressor; Veg (C)=vegC promoter; Veg (G)=vegG promote; lac=lac operator; SPA=staphylococcal protein A leader sequence; NPR=neutral protease leader sequence. Arrows indicate directions of gene expression.

Figure 2:
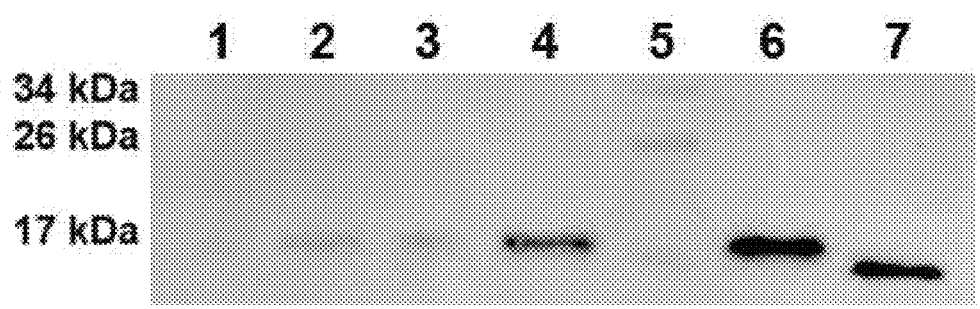
FIG. 2 is an image of a Western blot showing level of production of secretory hbFGF in different biological systems carrying different recombinant DNA constructs.

FIG. 2. Western Blot Analysis of Secretory hbFGF Expressed by Various DNA Constructs Culture supernatant samples of *B. subtilis* transformants harboring various DNA constructs (as specified in descriptions of various lanes below) grown under IPTG induction for different durations were analyzed for hbFGF expression. Lanes: (1) construct pVegGbFGF induced for 18 hr; (2) construct pVegCbFGF induced for 18 hr; (3) construct pVegGbFGF induced for 23 hr; (4) construct pVegCbFGF induced for 23 hr; (5) protein markers; (6) construct pCCQ induced for 8 hr; (7) construct pSO induced for 8 hr. All sample wells were loaded with 10 μl of culture supernatant containing the same number of cells.

Figure 3:
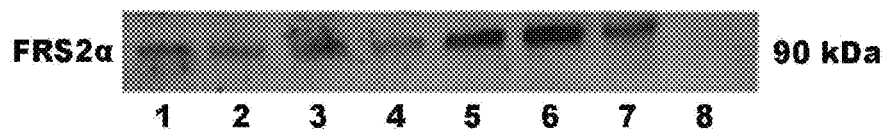
FIG. 3 is an image showing results of stimulation of C2C12 myoblasts by Mat-hbFGF.
Figure 3:

FIG. 3: Bioassay of Recombinant hbFGF.

Purification of recombinant hbFGF (rhbFGF) from an IPTG induced *B. subtilis* culture harboring plasmid pSO, and quantification of phosphorylated FRS2α formed in C2C12 myoblasts are described in Materials and methods. Different levels of FRS2α expressed by myoblast cells upon incubation with different quantities of commercial hbFGF (chbFGF) or rhbFGF are revealed by Western blotting using antibodies raised against (A) phosphotyrosine and (B) FRS2α (served as internal control). The two blots contain the same arrangement of antigens, with their quantities employed in the lanes being: [1] 1 μg chbFGF; [2] 0.7 μg chbFGF; [3] 0.5 μg chbFGF; [4] 0.1 μg chbFGF; [5] 0.5 μg rhbFGF; [6] 1 μg rhbFGF; [7] 0.1 μg of rhbFGF; [8] 150 μl of supernatant of a *B. subtilis* culture containing the CenA endoglucanase of *C. fimi* (served as a negative control).

Figure 4:
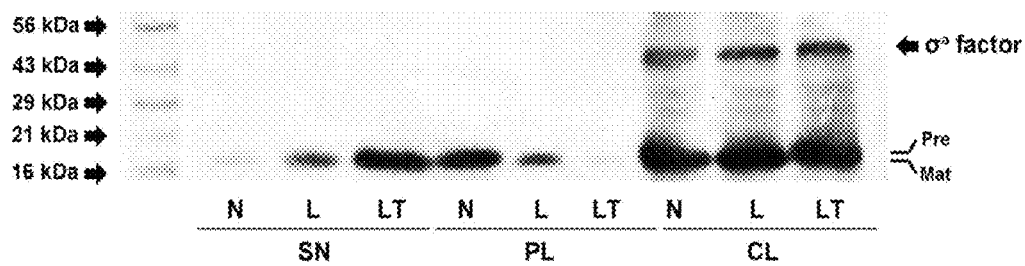
FIG. 4 is an image of a Western blot showing subcellular localization of Mat-bhFGF in *Bacillus subtilis* cultures harbouring plasmid pSO.

FIG. 4: Western Blot Analysis of Subcellular Localization of Mat-hbFGF in *B. subtilis* Cultures Harboring Plasmid pSO.

Induction and fractionation of cell cultures were done as described in Materials and methods. Before induction with IPTG for 11 hr, the cultures were subjected to one of the following three treatments: (i) without further processing (N), (ii) with a final concentration of 0.025 mg ml$^{-1}$ lysozyme (L), and (iii) with a final concentration of 0.025 mg ml$^{-1}$ lysozyme for 8 hrs., followed by an addition of a final concentration of 0.025% Triton X-100 (LT). All three types of cultures were then fractionated into: supernatant (SN), peptidoglycan (PL), and cell lysate (CL) samples. These samples were analyzed as shown in various lanes: M, protein markers; 1-3, SN; 4-6, PL; 7-9 CL; furthermore, the sources for these samples in various lanes: 1, 4 and 7 (N); 2, 5 and 8 (L); 3, 6 and 9 (LT), are also indicated. The amounts of SN and PL samples loaded were equal and prepared from cultures containing the same density of cells. The amount of CL [with RNA polymerase $\sigma^a$ factor included as internal control] loaded was 0.4 fold of SN to avoid overloading. Pre stands for premature hbFGF, whereas Mat represents mature hbFGF.

Figure 5:
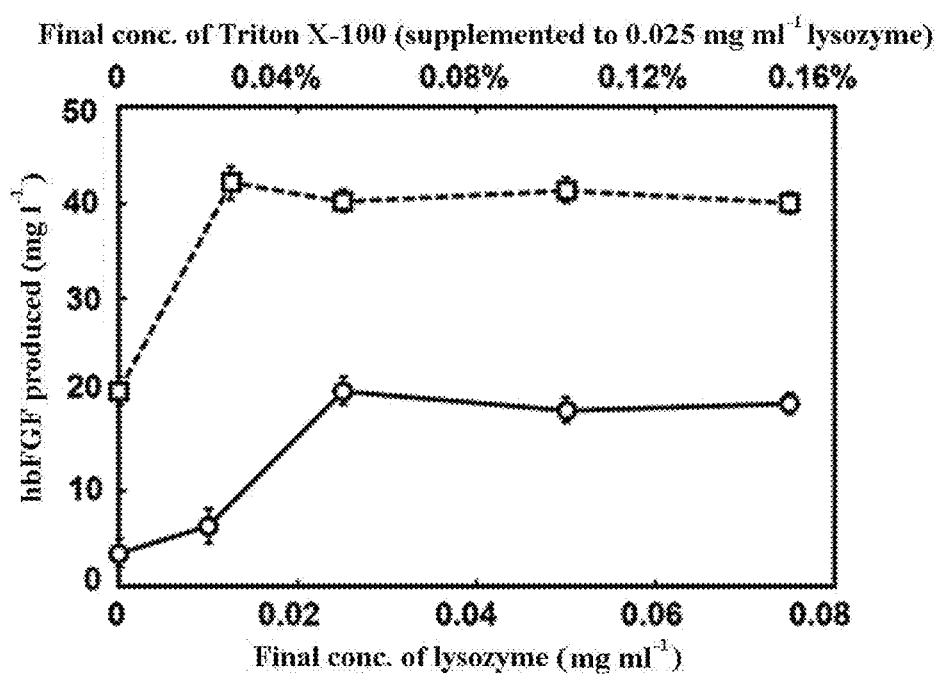
FIG. 5 is a graph showing effects of lysozyme and Triton X-100 on extracellular production of hbFGF from *Bacillus subtilis* cultures harbouring plasmid pSO.

FIG. 5. Effects of Lysozyme and Triton X-100 Treatments on Extracellular Production of hbFGF from *B. subtilis* Cultures Harboring Construct pSO All cultures involved were first grown under IPTG induction until an $A_{600}$ value reached 2. When lysozyme [L] was used alone, different quantities (mg ml$^{-1}$) of it were added individually and separately into the cultures to arrive at the final concentrations shown. The treatment was allowed to last for 11 hr. When the effect of supplementary Triton X-100 [T] was studied, subsequent to an initial treatment with 0.025 mg ml$^{-1}$ of L for 11 hours, the cultures were treated with different percentages (v/v) of T for 2 hr. The yields of hbFGF detected in the culture supernatants after treatments with different quantities of L (—O—) and L+T (-□-) are shown. The hbFGF yields were measured according to the protocol described in aforementioned Methods. The studies were each undertaken three times and standard error bars are shown.

Results

Engineering of DNA Constructs Expressing Secretory hbFGF

Initially, the synthetic hbfgf gene (Methods) was fused precisely and in-frame to the *Staphylococcal* Protein A (SPA) signal peptide under the regulation of two derivatives of the *B. subtilis* vegI promoter, the vegG and vegC promoters, which were individually harbored by the *B. subtilis/E. coli* shuttle vector, p184110Veg (Methods). Two resultant constructs, pVegGbFGF and pVegCbFGF (FIG. 1), were then obtained. Results from the earlier studies suggested that addition of the lacI$^q$ gene would facilitate inducible expression of the hbfgf gene. Therefore, the regulatory element was cloned into pVegCbFGF, which harbored the comparatively stronger vegC promoter, to yield plasmid pCCQ (FIG. 1). Moreover, studies have shown that other signal peptides would function more efficiently than that of SPA; thus the performance of the NPR signal peptide of a *B. amyloliquefaciens* protease gene was also evaluated. The SPA signal peptide was replaced by that of NPR in pCCQ to result in a new construct, designated pSO.

Expression of Secretory hbFGF by Various Constructs in *B. subtilis*

Expression of secretory hbFGF in *B. subtilis* transformants harboring the aforementioned four plasmids (FIG. 1) were examined by Western blot analysis. The results unequivocally demonstrated that culture media of the four transformants contained hbFGF activities, which, however, showed noticeable differences in: first, the level of hbFGF activity, and second, the size of the hbFGF product (FIG. 2). The first distinction was likely attributable to a combination of three factors: 1) variation in strength between the vegG and vegC promoters employed in the DNA constructs, 2) presence or not of the lacI$^q$ gene to facilitate inducible expression of the hbfgf gene, and 3) difference in efficiency between the SPA and NPR signal peptides to promote secretion of hbFGF. As for the second observation, however, the studies indicated that the differences were likely resulted from a variation at the site of peptidase cleavage between the signal peptide and hbFGF of the fusion products during secretion.

The ability of a signal peptide to enable hbFGF to acquire an authentic primary structure during secretion was the most critical consideration affecting the choice of DNA construct employed. In view that better yields of secretory hbFGF were obtainable from plasmids pCCQ and pSO (FIG. 2), these two constructs were selected for preparing hbFGF samples for protein sequencing and bioactivity analysis.

Protein Sequencing of Secreted hbFGFs

Secreted hbFGFs present in culture media of the two *B. subtilis* transformants carrying plasmids pCCQ and pSO were purified using heparin-agarose affinity chromatography (Methods). Protein sequencing of the two purified hbFGF products revealed distinctly different results, in which the factor encoded by plasmid pCCQ was shown to be a longer derivative, which contained ten extra amino acid residues of the SPA signal left at the N-terminus of mature native hbFGF (Mat-hbFGF; data not shown). On the other hand, when 313 peptides retrieved from a trypsin digest of hbFGF encoded by plasmid pSO were analyzed by mass spectrometry (aforementioned Methods), we were excited to note that analysis and reconstitution of the peptide sequencing results yielded the complete amino acid sequence of Mat-hbFGF (Please see Table 2 below). Moreover, the findings helped clarify why the two secreted hbFGF molecules exhibited different electrophoretic mobilities in Western blot analysis (FIG. 2).

Biological Assay of Mat-hbFGF Expressed by Plasmid pSO

The confirmation that Mat-hbFGF encoded by plasmid pSO in *B. subtilis* possessed an authentic primary structure (Table 2) prompted us to address whether the product was also bioactive. Stimulation of C2C12 myoblasts by Mat-hbFGF to form high levels of tyrosyl-phosphorylated FRS-2α supported that Mat-hbFGF was highly active, and that it was even more potent (about 3.5-fold) than its commercial counterpart (FIG. 3).

Expression of hbFGF Encoded by Plasmid pSO in *B. subtilis*

The demonstration that Mat-hbFGF possesses an authentic structure (Table 2) and potent bioactivity (FIG. 3) prompted us to undertake an elaborate study of its expression in *B. subtilis*. Western blot analysis of subcellular samples prepared from an IPTG induced culture carrying plasmid pSO revealed wide variation in distribution of hbFGF activity. Majority of the activity (ca. 98%) was shown to be present in the cytoplasm and the cell wall in roughly equal proportions, (FIG. 4, lane 7). The minute amount of residual activity (ca. 2%) was detected in the culture medium (FIG. 4, lane 1). This low level of extracellular Mat-hbFGF was estimated to have a concentration of 3.5 mg l$^{-1}$. When the activity in the periplasmic fraction was examined, it was unexpectedly to note that a 10- to 15-fold molar excess of Mat-hbFGF was found trapped in this narrow space (FIG. 4, lane 4).

Enhanced Secretion of Mat-hbFGF in *B. subtilis*

About 98% of hbFGF activity was detected to be trapped within the cell bound by the peptidoglycan. It was estimated that 83% of the activity was in the lysate, and half of it was Mat-hbFGF (FIG. 4, lane 7). The remaining 15% of the activity was trapped in the periplasm (FIG. 4, lane 4). The bound Mat-hbFGF represented a precious reserve for enhanced production of its secretory counterpart. Treating the cells with various cell wall weakening processes including sonication, pH adjustments, and exposure to ampicillin +/− glycine were all shown to be ineffective. When lysozyme was employed to treat the cell culture, the secretion of Mat-hbFGF was shown to be notably enhanced (FIG. 4, lane 2 and FIG. 5). Effects of various lysozyme concentrations and incubation conditions on the enhancement were further examined. It was found that addition of lysozyme in early log growth phase exhibited an inhibitory effect on cell growth, thus forcing hbFGF synthesis to a halt. On the other hand, treating cells with lysozyme in stationary phase showed no obvious effect on secretory production of Mat-hbFGF. Consequently, when a final concentration of 0.025 mg ml$^{-1}$ of lysozyme was added to log growth phase cells, maximum Mat-hbFGF secretion (ca. 20 mg l$^{-1}$; FIG. 5) was detected. Under these conditions, the cells maintained full viability (data not shown). Despite a 6-fold improvement, the treatment helped release only the polypeptide trapped in the periplasm (FIG. 4, lanes 4 and 5), but not its counterpart confined in the cell membrane (FIG. 4, lanes 7 and 8). Apparently, the lysozyme destabilized only the peptidoglycan but not the cell membrane. In addition, only less than 50% of the periplasmic Mat-hbFGF was effectively released (FIG. 4, lanes 4 and 5).

Subsequently, the effect of supplementary Triton X-100 on promoting release of Mat-hbFGF from the periplasm was studied. Log growth phase cells, which were previously treated with 0.025 mg ml$^{-1}$ of lysozyme (FIG. 5), were further incubated with different concentrations of Triton X-100 for various durations. It was found that a final concentration of 0.025% Triton X-100, which was added to the culture 2 hr prior to harvesting, provided the best result (FIG. 5). In summary, Triton X-100 treatment resulted in an additional 6-fold (>20 mg l$^{-1}$) increment, and a final overall yield of >40 mg l$^{-1}$, in secretory Mat-hbFGF (FIG. 5). In fact, virtually all the periplasmic Mat-hbFGF was released to the culture medium through the concerted effort of lysozyme and Triton X-100 (FIG. 4, lane 6).

TABLE 1

Primers used in aforementioned Methods. Also shown in Sequence Listing.

| Primer No. | SEQ ID No. | Sequence |
| --- | --- | --- |
| P1 | 1 | 5'-ACGATGAAGCTCAACAAAATGCTCCAGCCTTGCCAGAGGATGGCGGCAGCGG-3' |
| P2 | 2 | 5'-CCCGTTTTTGCAGTACAGGCGCTTTGGGTCCTTGAAGTGGCCTGGCGGGAAGGCGCCGCTGCCGCCATCCTCTGGCAAGG-3' |
| P3 | 3 | 5'-AAAGCGCCTGTACTGCAAAAACGGGGGCTTCTTCCTGCGCATCCACCCAGACGGCCGCGTTGACGGGGTCCGCGAGAAGA-3' |
| P4 | 4 | 5'-ATAGACACAACTCCGCGCTCTTCTGCTTGAAGTTGTAGCTTGATGTGAGGGTCGCTCTTCTCGCGGACCCCGTCAACGCG-3' |
| P5 | 5 | 5'-CAGAAGAGCGCGGAGTTGTGTCTATCAAAGGAGTGTGTGCTAACCGTTACCTGGCTATGAAGGAAGATGGACGCTTACTG-3' |
| P6 | 6 | 5'-TATTAGATTCCAAGCGTTCAAAAAAGAAACACTCATCCGTAACACATTTAGAAGCCAGTAAGCGTCCATCTTCCTTCATA-3' |
| P7 | 7 | 5'-TTTTTTGAACGCTTGGAATCTAATAACTACAATACTTACCGCTCACGCAAATACACCAGTTGGTATGTGGCACTGAAACG-3' |
| P8 | 8 | 5'-AGAAAGCTATCCTTTTTCTTCCAATGTCTGCTAAGAGCTAACTGCAGTTTTT-3' |
| P9 | 9 | 5'-AGAAAGCTATCCTTTTTCTTCCAATGTCTGCTAAGAGCTAACTGCAGTTTTT-3' |
| P10 | 10 | 5'-AAAAACTGCAGTTAGCTCTTAGCAGA-3' |
| P11 | 11 | 5'-GGGGGTACCTAATTTAAATTTTATTTGACAAAAATGGGCTCGTGTTGTCCAATAAATGTAGTGAGGTGG-3' |
| P12 | 12 | 5'-GGGGGTACCTAATTTAAATTTTATTTGACAAAAATGGGCTCGTGTTGTGCAATAAATGTAGTGAGGTGG-3' |
| P13 | 13 | 5'-CCGCCATCCTCTGGCAAGGCTGGAGCATTTTGTTGAGCTTCATCGTGTTGCGCAGCATTT-3' |
| P14 | 14 | 5'-TAATTTAAATTTTATTTGACAAAAATGGGCTCGTGTTGTCCAATAAATGTAGTGAGGTGGAATTGTGAGCGGAT-3' |
| P15 | 15 | 5'-GATGGTTAAACTCATAAAGGAAGCGGCGACAGCACTAGACAGTTTCTTACCTAAACCCATTTTTATCACCTCCTTTGTGAAATTGTTATC-3 |
| P16 | 16 | 5'-TCTAGTGCTGTCGCCGCTTCCTTTATGAGTTTAACCATCAGTCTGCCGGGTGTTCAGGCCCCAGCCTTGCCAGAGGATGGCGGCAGCGGC-3 |

TABLE 1-continued

Primers used in aforementioned Methods. Also shown in Sequence Listing.

| Primer No. | SEQ ID No. | Sequence |
|---|---|---|
| A | 17 | 5'-CCGGATCCGAATTCTAATTTAAATTTTATTTGACAAAAATGGGCTCGTGTT GTCCAATAAATGTAGTGAGGTGGAAAGGAGGTGATAAAA-3' |
| B | 18 | 5'-TTTTATCACCTCCTTTCCACCTCACTACATTTATTGGACAACACGAGCCCATTTTTGTCAAATAAAATTTAAATTAGAATTCGGATCCGG-3' |
| C | 19 | 5'-AAAGGAGGTGATAAAAGTGAAACCAAGTAACGTTATACGATGTCG-3' |
| D | 20 | 5'-GCGGATAGTTAATGATCAGCCCACTGACGCGTTGCGCGAG-3' |

TABLE 2

Analysis of purified hbFGF by liquid chromatography tandem mass spectrometry. Also shown in Sequence Listing.

| Peptide[a,b,c] | Mr(Calc)[d] | Mr(Expt)[e] | Ion Score | Homology |
|---|---|---|---|---|
| (1) PALPEDGGSG[10]AFPPGHFK | 1779.8580 | 1779.3254 | 74 | Identical |
| (2) PALPEDGGSG[10]AFPPGHFKDP[20]K | 2120.0327 | 2121.1582 | 9 | Matched |
| (3) RLYCKNGGF[30]FLR | 1529.7925 | 1531.2682 | 20 | Matched |
| (4) NGGF[30]FLR | 809.4184 | 808.7054 | 57 | Identical |
| (5) IHPDGRV[40]DGVR | 1219.6422 | 1220.0782 | 23 | Matched |
| (6) EKSDPH[50]IK | 952.4978 | 952.6254 | 7 | Matched |
| (7) SDPHIKLQLQAEER[60] | 1662.8689 | 1663.2682 | 48 | Identical |
| (8) [60]GVVSIKGVCA[70]NR | 1258.6816 | 1259.3054 | 50 | Identical |
| (9) YLAMKED[80]GR | 1081.5226 | 1082.3254 | 13 | Matched |
| (10) LLASKCVT[90]DECFFFER | 2020.9387 | 2019.9382 | 80 | Identical |
| (11) LE[100]SNNYNTYR | 1273.1254 | 1272.5734 | 72 | Identical |
| (12) LESNNYNTYRSR[110]K | 1643.8015 | 1643.1854 | 20 | Matched |
| (13) [110]KYTSWYVALK[120]R | 1414.7768 | 1414.6882 | 47 | Identical |
| (14) TGQYKLGSK[130]TGPGQK | 1548.8260 | 1548.9382 | 47 | Identical |
| (15) AILFL[140]PMSAK | 1090.0054 | 1089.6256 | 51 | Identical |
| (16) [130]TGPGQKAILFL[140]PMSAKS | 1744.9546 | 1744.8054 | 10 | Matched |

Notes:
[a]Subsequent to trypsin digestion of the purified hbFGF, a total of 313 peptides were identified by the Mascot search engine.
[b]The availability of Mat-hbFGF sequence in the literature has facilitated the selection and alignment of sequencing results of the trypsin digested peptides (16 of them as revealed in Table 2) to finally obtain a full sequence of the factor as shown below.
NH$_2$-PALPEDGGSG[10]AFPPGHFKDP[20]KRLYCKNGGF[30]FLRIHPDGRV[40]DGVREKSDPH[50]IKLQLQAEER[60]GVVSIKGVCA[70]NRYLAMKED[80]GRLLASKCVT[90]DECFFFERLE[100]SNNYNTYRSR[110]KYTSWYVALK[120]RTGQYKLGSK[130]TGPGQKAILFL[140]PMSAKS-COOH
[c]Five pairs of the trypsin digested peptides: (1) & (2), (3) & (4), (6) & (7), (11) & (12), and (15) & (16) shown to contain overlapping sequences.
[d]Theoretical mass-to-charge ratio of the peptide.
[e]The experimental mass-to-charge ratio of the peptide.

Discussion

Studies leading to the present invention had shown that one of the skin growth factors, i.e. hEGF, can be efficiently expressed by our research group in both *E. coli* and *B. subtilis* using approaches we had designed. Due to the exceptionally high yields of excretory production of hEGF in *E. coli*, the same approaches used to produce hEGF for commercial applications were used to produce hbFGF. However, the same approaches have not been shown effective in producing hbFGF. Presumably, the poor performance resulted from inefficient secretion or/and excretion of hbFGF in *E. coli*. This might explain why recombinant hbFGF has been prevalently produced by intracellular expression.

In the studies leading to the present invention, biologic host systems including yeasts, insect and mammalian cells have also been employed to express hbFGF. Although hbFGF products derived from *E. coli* and other host systems are often shown to exhibit some degree of bioactivity, they are commonly expressed as hbFGF derivatives and not authentic hbFGF.

One aspect of the present invention is concerned with making use of *B. subtilis* as a biological system for production of hbFGF. Although *B. subtilis* is reckoned as a GRAS organism and has been employed as a host for the expression of a variety of proteins, prior to the present invention the application of *B. subtilis* for the expression of hbFGF has so far been unsuccessful commercially or pharmaceutically.

From the aforementioned illustration, it is shown that *B. subtilis* was successfully applied to express medically valuable proteins, it was envisaged that a step by step approach might be adopted to overcome the difficulties encountered in secretory hbFGF expression in this host. Our studies have shown that a protease-free environment, efficient transcription and effective secretion would facilitate the target expression. The detection of hbFGF in our studies shows that two vegetative promoters, vegC and vegG, employed in the study (FIG. 1) can contribute to effective results, with the former promoter performing more efficiently than the latter promoter (FIG. 2). The results also substantiated that hbFGF is secretable in *B. subtilis*, despite the heterogeneity in size of the two secreted hbFGF products (FIG. 2). The findings supported the notion that the two hbFGF products possessed different N-termini, which resulted likely from peptidase cleavage that took place at different positions relative to the N-terminal amino acid of Mat-hbFGF in the premature products.

The results obtained from protein sequencing confirmed that Mat-hbFGF encoded by plasmid pSO in *B. subtilis* shares the same sequence with its native counterpart (Table 2). The information also helped us decide that pSO was the final DNA construct to be employed for further study of hbFGF expression in *B. subtilis*. To our knowledge, our work represents the first demonstration of successful expression of hbFGF in *B. subtilis*; it also presents the first illustration of expression of authentic Mat-hbFGF directly from a recombinant host system.

The vegC promoter, lacI$^q$ gene and npr secretion leader sequence engineered in plasmid pSO (FIG. 1) are all important elements for successful expression of authentic Mat-hbFGF in *B. subtilis*. Moreover, the reasonably high level of hbFGF encoded by plasmid pSO even under shake flask conditions greatly facilitated the investigation of subcellular distribution of hbFGF during secretory expression. However, we were discontented with the low level of secreted Mat-hbFGF (FIG. 2, lane 7), which was ca. 3.5 mg l$^{-1}$ and represented only 2% of the overall expression. The low efficiency of Mat-hbFGF export, which could be easily worsened by complications such as low transcriptional efficiency, plasmid instability and active proteolysis, might account for the difficulties faced previously by other groups in secretory expression of hbFGF in *B. subtilis*. The detection of high levels of Mat-hbFGF in both the periplasm and the cell lysate of *B. subtilis* (FIG. 4) supported the notion that some of the trapped product could be released to the culture medium. The membrane destabilization method introduced in this study worked well to release virtually all Mat-hbFGF from the periplasmic space (FIG. 4, lane 6), although it was not quite effective in releasing the factor caught in the membrane (FIG. 4, lane 9). Moreover, the lysozyme performed well in releasing Mat-hbFGF from only log but not other growth phase cells (data not shown). The factor freed from the periplasm was later confirmed to possess not only bioactivity but also the authentic primary structure (data not shown). Therefore, Mat-hbFGF is likely retained in the periplasm by the peptidoglycan layer right after its translocation through the secretion channels at the plasma membrane. Apparently, the lysozyme acts particularly well on a growing peptidoglycan rather than on a fully assembled one. On the other hand, Triton X-100 appears to complement the action of lysozyme; it works well on stationary-phase cells to weaken the peptidoglycan. Therefore, a combined use of the two chemicals, together with optimized treatment conditions, resulted in an astounding 12-fold increase (from 3.5 mg l$^{-1}$ to >40 mg l$^{-1}$) in the yield of secreted Mat-hbFGF (FIG. 4 and FIG. 5).

Although Mat-hbFGF had been shown to be a medically versatile protein (for example in healing various skin wounds and promoting angiogenesis), using it commercially had not been realistically possible. Now with the aforementioned means and methods for producing Mat-hbFGF cost effectively, the application of authentic Mat-hbFGF in different contexts will become possible.

It should be understood that certain features of the invention, which are, for clarity, described in the content of separate embodiments, examples or experiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose. Examples of this prior art are listed out in the below list of references, contents of which are incorporated in their entirety.

REFERENCES

1. Wong, S. L. Advances in the use of *Bacillus subtilis* for the expression and secretion of heterologous proteins. *Curr. Opin. Biotechnol.* 6, 517-522 (1995).
2. Wong, S. L., Ye, R. & Nathoo, S. Engineering and production of streptokinase in a *Bacillus subtilis* expression-secretion system. *Appl. Environ. Microbiol.* 60, 517-523 (1994).
3. Özdamar, T. H. et al. Expression system for recombinant human growth hormone production from *Bacillus subtilis*. *Biotechnol. Prog.* 25, 75-84 (2009).
4. Simonen, M. & Palva, I. Protein secretion in *Bacillus* species. *Microbiol. Rev.* 57, 109-137 (1993).
5. Westers, L., Dijkstra, D. S., Westers, H., van Dijl, J. M. & Quax, W. J. Secretion of functional human interleukin-3 from *Bacillus subtilis*. *J. Biotechnol.* 123, 211-224 (2006).
6. Palva, I. et al. Secretion of Interferon by *Bacillus subtilis*. *Gene* 22, 229-235 (1983).

7. Lam, K. H., Chow, K. C. & Wong, W. K. Construction of an efficient *Bacillus subtilis* system for extracellular production of heterologous proteins. *J. Biotechnol* 63, 167-177 (1998).
8. Nakayama, A. et al. Efficient secretion of the authentic mature human growth hormone by *Bacillus subtilis*. *J. Biotechnol.* 8, 123-134 (1988).
9. Ferrer-Miralles, N., Domingo-Espín, J., Corchero, J. L., Vázquez, E. & Villayerde, A. Microbial factories for recombinant pharmaceuticals. *Microb. Cell Fact.* 8, 17 (2009).
10. Westers, L., Westers, H. & Quax, W. J. *Bacillus subtilis* as cell factory for pharmaceutical proteins: a biotechnological approach to optimize the host organism. *Biochim. Biophys. Acta* 1694, 299-310 (2004).
11. Leung, L. et al. Human epidermal growth factor enhances healing of diabetic foot ulcers. *Diabetes Care* 26, 1856-61 (2003).
12. Wong, W. K. R., Lam, K. H. & Tsang, M.-W. Method and composition for treating skin wounds with epidermal growth factor. U.S. Pat. No. 7,517,528 (2009).
13. Tsang, M. W., Tsang, K. Y. & Wong, W. K. R. The use of recombinant human epidermal growth factor (rhEGF) in a gentleman with drug-induced Steven Johnson syndrome. *Dermatol. Online J* 10, 25 (2004).
14. Sivakesava, S. et al. Production of excreted human epidermal growth factor (hEGF) by an efficient recombinant *Escherichia coli* system. *Proc. Biochem.* 34, 893-900 (1999).
15. Haldenwang W G. 1995 The sigma factors of *Bacillus subtilis*. Microbiol. rev. 59:1-30.
16. Huang, R. et al. Human epidermal growth factor excreted by recombinant *Escherichia coli* K-12 has the correct N-terminus and is fully bioactive. *Proc. Biochem.* 35, 1-5 (1999).
17. Wong, W. K. R., Fu, Z., Wang, Y. Y., Ng, K. L. & Chan, A. K. N. Engineering of efficient *Escherichia coli* excretion systems for the production of heterologous proteins for commercial applications. *Renct. Pat. Chem. Eng.* 5, 45-55 (2012).
18. Bikfalvi, A., Klein, S., Pintucci, G. & Rifkin, D. B. Biological roles of fibroblast growth factor-2. *Endocr. Rev.* 18, 26-45 (1997).
19. Barr, P. J. et al. Expression and processing of biologically active fibroblast growth factors in the yeast *Saccharomyces cerevisiae*. *J. Biol. Chem.* 263,16471-16478 (1988).
20. Mirzahoseini, H., Mehraein, F., Omidinia, E. & Razavi, M. R. Differential expression of human basic fibroblast growth factor in *Escherichia coli*: potential role of promoter. *World J. Microbiol. Biotechnol.* 20, 161-165 (2004).
21. Mu, X. et al. High-level expression, purification, and characterization of recombinant human basic fibroblast growth factor in *Pichia pastoris*. *Protein Expr. Purif.* 59, 282-288 (2008).
22. Garke, G., Deckwer, W.-D. & Anspach, F. B. Preparative two-step purification of recombinant human basic fibroblast growth factor from high-cell-density cultivation of *Eschericia coli*. *J. Chromatogr. B: Analyt Technol Biomed Life Sci.* 737, 25-38 (2000).
23. FGF2 Sf9 recombinant protein. *Mybiosource* at <http://www.mybiosource.com/datasheet.php?products_id=142242>
24. FGF2 (NM_002006) Purified Human Protein. at <http://www.origene.com/protein/TP317426/FGF2.aspx>
25. Alibolandi, M. & Mirzahoseini, H. Purification and refolding of overexpressed human basic fibroblast growth factor in *Escherichia coli*. *Biotechnol. Res. Int.* 2011, 1-6 (2011).
26. Xu, C. et al. Basic fibroblast growth factor supports undifferentiated human embryonic stem cell growth without conditioned medium. *StemCells* 23, 315-323 (2005).
27. Khurana, R. & Simons, M. Insights from angiogenesis trials using fibroblast growth factor for advanced arteriosclerotic disease. *TrendsCardiovas. Med.* 13, 116-122 (2003).
28. Sellke, F. W., Laham, R. J., Edelman, E. R., Pearlman, J. D. & Simons, M. Therapeutic angiogenesis with basic fibroblast growth factor: technique and early Results. *Ann. Thorac. Surg.* 65, 1540-1544 (1998).
29. Biocompare: Basic Fibroblast Growth Factor. at <http://www.biocompare.com/Search-Biomolecules/?search=basic+fibroblast+growth+factor>
30. WU, D., Wang, Y., Gu, Q. & Wu, C. Basic fibroblast growth factor expressed in *Bacillus Subtilis* BS224. *Lett. Biotechnol.* 13,439-442 (2002).
31. Wang, Y. et al. Efficient *Bacillus subtilis* promoters for graded expression of heterologous genes in *Escherichia coli*. *Res. J. Biotechnol.* 5, 5-14 (2010).
32. Lam, T. L., Wong, R. S.C. & Wong, W. K. R. Enhancement of extracellular production of a *Cellulomonas fimi* exoglucanase in *Escherichia coli* by the reduction of promoter strength. *Enzyme Microb. Technol.* 20, 482-488 (1997).
33. Wong, W. K. R. & Sutherland, M. L. Excretion of heterologous proteins from *E. coli*. U.S. Pat. No. 5,646,015 (1997).
34. Kontaridis, M. I., Liu, X., Zhang, L. & Bennett, A. M. Role of SHP-2 in fibroblast growth factor receptor-mediated suppression of myogenesis in C2C12 myoblasts. *Mol. Cell. Biol.* 22, 3875-3891 (2002).
35. Sheng, Z., Chang, S. B. & Chirico, W. J. Expression and purification of a biologically active basic fibroblast growth factor fusion protein. *Protein Expr. Purif.* 27, 267-271 (2003).
36. Andrades, J. A. et al. Production of a recombinant human basic fibroblast growth factor with a collagen binding domain. *Protoplasma* 218, 95-103 (2001).
37. McGee, G. S. et al. Recombinant basic fibroblast growth factor accelerates wound healing. *J. of Surg. Res.* 45, 145-153 (1988).
38. Rose, R. E. The nucleotide sequence of pACYC184. *Nucleic Acids Res* 16, 355 (1988).
39. Bernardi, A. & Bernardi, F. Complete sequence of pSC101. *Nucl. Acids Res.* 12, 9415-9426 (1984).
40. Wong, D. K. H. et al. Extracellular expression of human epidermal growth factor encoded by an *Escherichia coli* K-12 plasmid stabilized by the ytl2-incR system of *Salmonella typhimurium*. *J. Ind. Microbiol. Biotechnol.* 21, 31-36 (1998).
41. Bae, T. & Schneewind, O. The YSIRK-G/S motif of *Staphylococcal* protein A and its role in efficiency of signal peptide processing. *J. Bacteriol.* 185, 2910-2919 (2003).
42. Asubel, F. et al. *Current protocols in molecular biology.* vol. 2. New York: Wiley, 1993:11.2.1-11.2.5.
43. Schagger, H. & Von Jagow, G. Tricine-sodium dodecyl sulfate-polyacrylamide gel electrophoresis for the separation of proteins in the range from 1 to 100 kDa. *Anal. Chem.* 166, 368-379 (1987).

The invention claimed is:

1. A method for production of authentic human basic fibroblast growth factor (hbFGF) protein by a host, wherein the authentic human basic fibroblast growth factor (hbFGF) has a sequence consisting of SEQ ID NO:37, said method comprising:
    a) providing *Bacillus subtilis* as the host;
    b) preparing a recombinant DNA construct with an insert including a first VegC promoter, lac$^q$ operator, a second VegC promoter and DNA coding for said authentic human basic fibroblast growth factor;
    c) introducing said DNA construct in the host for expression of said authentic human basic fibroblast growth factor protein;
    d) allowing said *Bacillus subtilis* to grow in a cell culture and express said authentic human basic fibroblast growth factor protein;
    e) allowing said *Bacillus subtilis* to secrete said authentic human basic fibroblast growth factor protein in the cell culture; and
    f) collecting said secreted authentic human basic fibroblast growth factor protein from the cell culture.

2. The method as claimed in claim 1, comprising a step of facilitating export of said authentic human basic fibroblast growth factor protein to the cell culture in which said host suspends.

3. The method as claimed in claim 1, comprising a step of positioning a neutral protease leader sequence (NPR) between said second VegC promoter and said DNA coding for authentic human basic fibroblast growth factor protein.

4. The method as claimed in claim 3, wherein said insert consists of, and in the sequence of, said first VegC promoter, said lac$^q$ operator, said second VegC promoter, said neutral protease leader sequence and said DNA coding for authentic human basic fibroblast growth factor protein.

5. The method as claimed in claim 1, comprising, a step of, during the production of said authentic human basic fibroblast growth factor protein, treating said host with lysozyme.

6. The method as claimed in claim 5, wherein said treating of said host with lysozyme is conducted when said host is at log growth phase.

7. The method as claimed in claim 5, wherein said host is treated with 0.025-0.1 mg/ml of said lysozyme.

8. The method as claimed in claim 5, comprising a step of treating said host with Triton X-100.

9. The method as claimed in claim 8, wherein said host is treated with 0.025-0.08% of Triton X-100.

10. The method as claimed in claim 9, wherein said treatment by said Triton X-100 is performed during stationary-phase of said host.

11. The method as claimed in claim 2 comprising, without having to concentrate said culture, a step of harvesting at least 30-43 mg/l of said human basic fibroblast growth factor protein from said culture.

* * * * *

SEQUENCE LISTING

<160> NUMBER OF SEQ ID NOS: 37

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgatgaagc tcaacaaaat gctccagcct tgccagagga tggcggcagc gg            52

<210> SEQ ID NO 2
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2 cccgttttg cagtacaggc gctttgggtc cttgaagtgg cctggcggga aggcgccgct     60
gccgccatcc tctggcaagg                                                80

<210> SEQ ID NO 3
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaagcgcctg tactgcaaaa acgggggctt cttcctgcgc atccacccag acggccgcgt    60
tgacggggtc cgcgagaaga                                                80

<210> SEQ ID NO 4
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atagacacaa ctccgcgctc ttctgcttga agttgtagct tgatgtgagg gtcgctcttc    60
tcgcggaccc cgtcaacgcg                                                80

<210> SEQ ID NO 5
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagaagagcg cggagttgtg tctatcaaag gagtgtgtgc taaccgttac ctggctatga    60
aggaagatgg acgcttactg                                                80

<210> SEQ ID NO 6
<211> LENGTH: 80
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 6
tattagattc caagcgttca aaaagaaac actcatccgt aacacattta gaagccagta    60
agcgtccatc ttccttcata                                              80

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7 tttttttgaac gcttggaatc taataactac aatacttacc gctcacgcaa atacaccagt    60
tggtatgtgg cactgaaacg                                              80

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaggatagct ttctgcccag gtcctgtttt ggatccaagt ttatactgcc cagtgcgttt    60
cagtgccaca taccaactgg                                              80

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agaaagctat cctttttctt ccaatgtctg ctaagagcta actgcagttt tt           52

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaaactgca gttagctctt agcaga                                       26

<210> SEQ ID NO 11
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggggtacct aatttaaatt ttatttgaca aaaatgggct cgtgttgtcc aataaatgta    60

-continued

```
<210> SEQ ID NO 12
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12 ggggtacct aatttaaatt ttatttgaca aaaatgggct cgtgttgtgc aataaatgta      60
gtgaggtgg                                                             69

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgccatcct ctggcaaggc tggagcattt tgttgagctt catcgtgttg cgcagcattt      60

<210> SEQ ID NO 14
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taatttaaat tttatttgac aaaaatgggc tcgtgttgtc aataaatgt agtgaggtgg       60 aattgtgagc ggat                                                       74

<210> SEQ ID NO 15
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gatggttaaa ctcataaagg aagcggcgac agcactagac agtttcttac ctaaacccat      60
ttttatcacc tcctttgtga aattgttatc                                      90

<210> SEQ ID NO 16
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tctagtgctg tcgccgcttc ctttatgagt ttaaccatca gtctgccggg tgttcaggcc      60
ccagccttgc cagaggatgg cggcagcggc                                      90

<210> SEQ ID NO 17
<211> LENGTH: 90
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccggatccga attctaattt aaattttatt tgacaaaaat gggctcgtgt tgtccaataa      60
atgtagtgag gtggaaagga ggtgataaaa                                      90

<210> SEQ ID NO 18
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttttatcacc tcctttccac ctcactacat ttattggaca acacgagccc attttgtca      60 aataaaattt aaattagaat tcggatccgg                                      90

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaaggaggtg ataaaagtga aaccaagtaa cgttatacga tgtcg                     45

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcggatagtt aatgatcagc ccactgacgc gttgcgcgag                           40

<210> SEQ ID NO 21
<211> LENGTH: 18
<212> TYPE: PRT
<213> ORGANISM: Homo sapiens

<400> SEQUENCE: 21

Pro Ala Leu Pro Glu Asp Gly Gly Ser Gly Ala Phe Pro Pro Gly His
1               5                   10                  15

Phe Lys

<210> SEQ ID NO 22
<211> LENGTH: 21
<212> TYPE: PRT
<213> ORGANISM: Homo sapiens

<400> SEQUENCE: 22

Pro Ala Leu Pro Glu Asp Gly Gly Ser Gly Ala Phe Pro Pro Gly His
1               5                   10                  15

Phe Lys Asp Pro Lys
            20
```

```
<210> SEQ ID NO 23
<211> LENGTH: 12
<212> TYPE: PRT
<213> ORGANISM: Homo sapiens

<400> SEQUENCE: 23

Arg Leu Tyr Cys Lys Asn Gly Gly Phe Phe Leu Arg
1               5                   10

<210> SEQ ID NO 24
<211> LENGTH: 7
<212> TYPE: PRT
<213> ORGANISM: Homo sapiens

<400> SEQUENCE: 24

Asn Gly Gly Phe Phe Leu Arg
1               5

<210> SEQ ID NO 25
<211> LENGTH: 11
<212> TYPE: PRT
<213> ORGANISM: Homo sapiens

<400> SEQUENCE: 25

Ile His Pro Asp Gly Arg Val Asp Gly Val Arg
1               5                   10

<210> SEQ ID NO 26
<211> LENGTH: 8
<212> TYPE: PRT
<213> ORGANISM: Homo sapiens

<400> SEQUENCE: 26

Glu Lys Ser Asp Pro His Ile Lys
1               5

<210> SEQ ID NO 27
<211> LENGTH: 14
<212> TYPE: PRT
<213> ORGANISM: Homo sapiens

<400> SEQUENCE: 27

Ser Asp Pro His Ile Lys Leu Gln Leu Gln Ala Glu Glu Arg
1               5                   10

<210> SEQ ID NO 28
<211> LENGTH: 12
<212> TYPE: PRT
<213> ORGANISM: Homo sapiens

<400> SEQUENCE: 28

Gly Val Val Ser Ile Lys Gly Val Cys Ala Asn Arg
1               5                   10

<210> SEQ ID NO 29
<211> LENGTH: 9
<212> TYPE: PRT
<213> ORGANISM: Homo sapiens

<400> SEQUENCE: 29

Tyr Leu Ala Met Lys Glu Asp Gly Arg
1               5
```

```
<210> SEQ ID NO 30
<211> LENGTH: 16
<212> TYPE: PRT
<213> ORGANISM: Homo sapiens

<400> SEQUENCE: 30

Leu Leu Ala Ser Lys Cys Val Thr Asp Glu Cys Phe Phe Phe Glu Arg
1               5                   10                  15

<210> SEQ ID NO 31
<211> LENGTH: 10
<212> TYPE: PRT
<213> ORGANISM: Homo sapiens

<400> SEQUENCE: 31

Leu Glu Ser Asn Asn Tyr Asn Thr Tyr Arg
1               5                   10

<210> SEQ ID NO 32
<211> LENGTH: 13
<212> TYPE: PRT
<213> ORGANISM: Homo sapiens

<400> SEQUENCE: 32

Leu Glu Ser Asn Asn Tyr Asn Thr Tyr Arg Ser Arg Lys
1               5                   10

<210> SEQ ID NO 33
<211> LENGTH: 11
<212> TYPE: PRT
<213> ORGANISM: Homo sapiens

<400> SEQUENCE: 33

Lys Tyr Thr Ser Trp Tyr Val Ala Leu Lys Arg
1               5                   10

<210> SEQ ID NO 34
<211> LENGTH: 15
<212> TYPE: PRT
<213> ORGANISM: Homo sapiens

<400> SEQUENCE: 34

Thr Gly Gln Tyr Lys Leu Gly Ser Lys Thr Gly Pro Gly Gln Lys
1               5                   10                  15

<210> SEQ ID NO 35
<211> LENGTH: 10
<212> TYPE: PRT
<213> ORGANISM: Homo sapiens

<400> SEQUENCE: 35

Ala Ile Leu Phe Leu Pro Met Ser Ala Lys
1               5                   10

<210> SEQ ID NO 36
<211> LENGTH: 17
<212> TYPE: PRT
<213> ORGANISM: Homo sapiens

<400> SEQUENCE: 36

Thr Gly Pro Gly Gln Lys Ala Ile Leu Phe Leu Pro Met Ser Ala Lys
1               5                   10                  15

Ser
```

```
<210> SEQ ID NO 37
<211> LENGTH: 146
<212> TYPE: PRT
<213> ORGANISM: Homo sapiens

<400> SEQUENCE: 37

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
            35                  40                  45

Pro His Ile Lys Leu Gln Leu Gln Ala Glu Glu Arg Gly Val Val Ser
        50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145
```